(12) United States Patent
Qiao et al.

(10) Patent No.: US 11,373,758 B2
(45) Date of Patent: Jun. 28, 2022

(54) COGNITIVE ASSISTANT FOR AIDING EXPERT DECISION

(71) Applicant: International Business Machines Corporation, Armonk, NY (US)

(72) Inventors: Mu Qiao, Belmont, CA (US); Dylan Fitzpatrick, Belmont, CA (US); Ramani Routray, San Jose, CA (US); Divyesh Jadav, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 483 days.

(21) Appl. No.: 16/126,559

(22) Filed: Sep. 10, 2018

(65) Prior Publication Data

US 2020/0082940 A1   Mar. 12, 2020

(51) Int. Cl.
*G16H 50/20* (2018.01)
*G16H 10/60* (2018.01)
(Continued)

(52) U.S. Cl.
CPC .............. *G16H 50/20* (2018.01); *G06N 5/043* (2013.01); *G06N 20/00* (2019.01); *G16H 10/60* (2018.01)

(58) Field of Classification Search
CPC ........ G16H 50/20; G16H 10/60; G06N 20/00; G06N 5/043; G06N 3/08; G06N 3/0445;
(Continued)

(56) References Cited

U.S. PATENT DOCUMENTS

| 2006/0112050 A1* | 5/2006 | Miikkulainen ........ G16H 50/20 706/46 |
| 2013/0198207 A1* | 8/2013 | Dolan ................... G06F 16/245 707/749 |

(Continued)

FOREIGN PATENT DOCUMENTS

| WO | WO-2014052921 A2 * | 4/2014 | ............. G06Q 10/10 |
| WO | WO-2018211140 A1 * | 11/2018 | .............. G06N 3/08 |
| WO | WO-2019211089 A1 * | 11/2019 | ............. G16H 50/70 |

OTHER PUBLICATIONS

Trang Pham et al. "Predicting healthcare trajectories from medical records: A deep learning approach", Journal of Biomedical Informatics 69 (2017) 218-229. https://reader.elsevier.com/reader/sd/pii/S15320464173007 (Year: 2017).*

*Primary Examiner* — Fonya M Long
*Assistant Examiner* — Alaaeldin M Elshaer
(74) *Attorney, Agent, or Firm* — Patterson + Sheridan, LLP

(57) ABSTRACT

Intelligent cognitive assistants for decision-making are provided. A first plurality of decisions made by a first healthcare provider during treatment of a first patient is monitored. For each respective decision of the first plurality of decisions, one or more corresponding medical attributes of the first patient that were present at a time when the respective decision was made are determined. A cognitive assistant is trained, using an imitation learning model, based on each of the first plurality of decisions and the corresponding one or more medical attributes of the first patient. Subsequently, one or more medical attributes of a second patient are received, and a first medical decision is generated by processing the one or more medical attributes of the second patient using the cognitive assistant.

20 Claims, 6 Drawing Sheets

(51) Int. Cl.
*G06N 20/00* (2019.01)
*G06N 5/04* (2006.01)
*G06N 5/02* (2006.01)

(58) Field of Classification Search
CPC ........ G06N 3/0454; G06N 3/088; G06N 5/02;
G06N 3/04; G06N 3/00; G06F 9/00;
A61B 5/00; G06Q 50/24
USPC ........................................................ 705/2, 3
See application file for complete search history.

(56) References Cited

U.S. PATENT DOCUMENTS

| | | |
|---|---|---|
| 2014/0316220 A1 | 10/2014 | Sheldon |
| 2015/0019241 A1 | 1/2015 | Bennett et al. |
| 2018/0025127 A1 | 1/2018 | Bagchi et al. |
| 2018/0068082 A1 | 3/2018 | Brown et al. |

* cited by examiner

US 11,373,758 B2

COGNITIVE ASSISTANT FOR AIDING EXPERT DECISION

BACKGROUND

The present invention relates to sequential decision-making, and more specifically, to training cognitive models to provide guidance for expert decision-making.

In a wide variety of fields, expert decision-making based on careful consideration of all available data is vital to ensure high quality results. This is particularly true in healthcare, where medical decisions are made based on years of training and experience in order to ensure optimal patient outcomes. However, due to the significant time and expense involved in attaining such expertise, access to care can be limited, and inefficiencies can arise. For example, in order to reach a diagnosis, a sequence of decisions determines how much time passes before diagnosis, how costly the trajectories are, and the like. Further, in some instances, a subject-matter expert may be unavailable to provide guidance at each inflection point. This causes unnecessary delays and inefficiencies, which may lead to sub-optimal care.

SUMMARY

According to one embodiment of the present disclosure, a method is provided. The method includes monitoring a first plurality of decisions made by a first healthcare provider during treatment of a first patient. The method further includes determining, for each respective decision of the first plurality of decisions, one or more corresponding medical attributes of the first patient that were present at a time when the respective decision was made. Additionally, the method includes training a cognitive assistant, using an imitation learning model, based on each of the first plurality of decisions and the corresponding one or more medical attributes of the first patient. The method also includes subsequently receiving one or more medical attributes of a second patient, and generating a first medical decision by processing the one or more medical attributes of the second patient using the cognitive assistant.

According to a second embodiment of the present disclosure, a computer program product is provided. The computer program product includes a computer-readable storage medium having computer-readable program code embodied therewith, the computer-readable program code executable by one or more computer processors to perform an operation. The operation includes monitoring a first plurality of decisions made by a first healthcare provider during treatment of a first patient. The operation further includes determining, for each respective decision of the first plurality of decisions, one or more corresponding medical attributes of the first patient that were present at a time when the respective decision was made. Additionally, the operation includes training a cognitive assistant, using an imitation learning model, based on each of the first plurality of decisions and the corresponding one or more medical attributes of the first patient. The operation also includes subsequently receiving one or more medical attributes of a second patient, and generating a first medical decision by processing the one or more medical attributes of the second patient using the cognitive assistant.

According to a third embodiment of the present disclosure, a system is provided. The system includes one or more computer processors, and a memory containing a program which when executed by the one or more computer processors performs an operation. The operation includes monitoring a first plurality of decisions made by a first healthcare provider during treatment of a first patient. The operation further includes determining, for each respective decision of the first plurality of decisions, one or more corresponding medical attributes of the first patient that were present at a time when the respective decision was made. Additionally, the operation includes training a cognitive assistant, using an imitation learning model, based on each of the first plurality of decisions and the corresponding one or more medical attributes of the first patient. The operation also includes subsequently receiving one or more medical attributes of a second patient, and generating a first medical decision by processing the one or more medical attributes of the second patient using the cognitive assistant.

DETAILED DESCRIPTION

Figure 1:
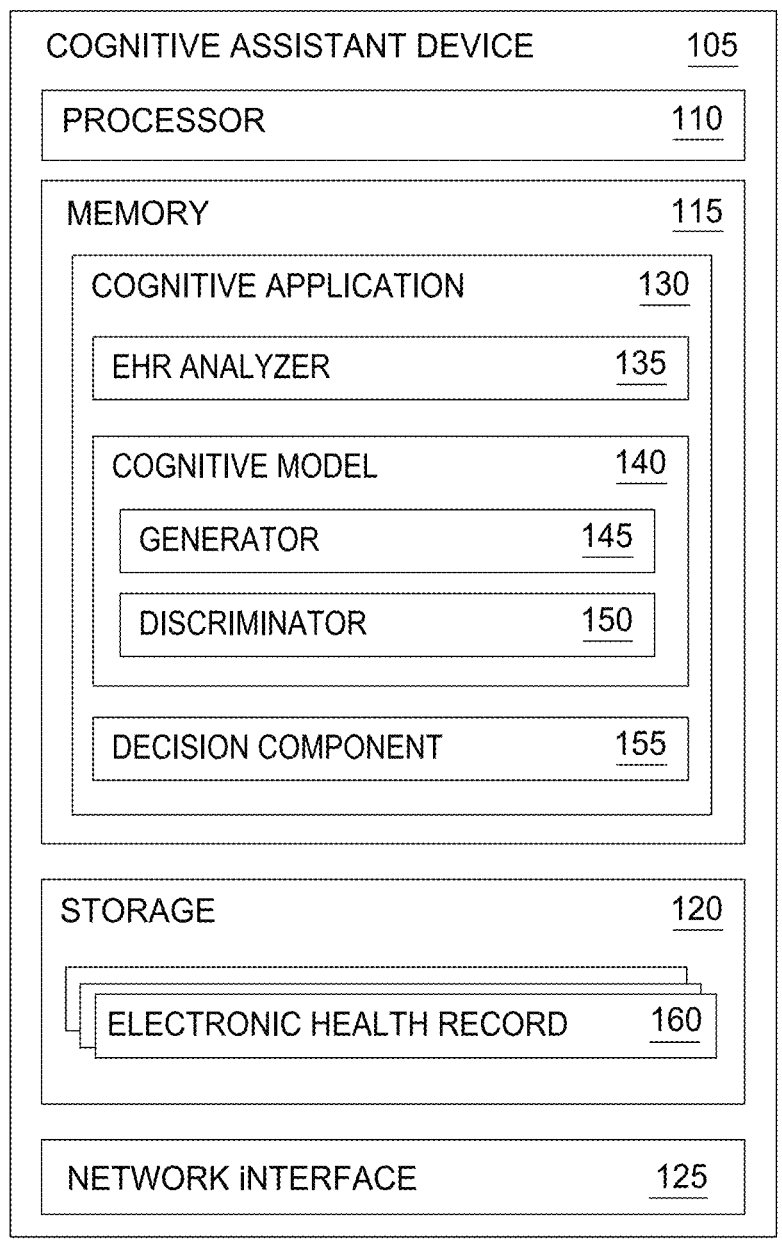
FIG. 1 is a block diagram of a cognitive assistant device, according to one embodiment disclosed herein.

Embodiments of the present disclosure provide techniques for the training and use of a cognitive machine learning model to facilitate decision making based on prior expert exemplar decisions. In one embodiment, an imitation learning model is trained based on expert trajectories or decisions. This model can then be used to generate high-quality suggestions and decisions for subsequent cases and states. In one embodiment, this model is utilized to aid the decision-making process of a subject-matter expert (SME), such as by suggesting high-quality decisions. In another embodiment, the model generates decisions to guide less experienced individuals in their decision-making. In at least one embodiment, the cognitive model is utilized to both generate and enact decisions. In some embodiments, the results of these decisions, if implemented, can similarly be ingested in order to determine the best decision for the new resulting state. In this way, embodiments of the present disclosure reduce inefficiencies and costs involved in decision-making, and improve the quality of decisions through objective models that utilize criteria that includes far more data than previously considered.

In embodiments, the cognitive assistant is trained based on previous decisions from SMEs. In some embodiments, multiple cognitive assistants may be trained for distinct fields or problems, based on input from SMEs corresponding to each field. For example, in some healthcare embodiments, distinct cognitive models are trained using data corresponding to distinct cohorts of patients. Similarly, in some embodiments, the pool of SMEs used to train each cognitive assistant may vary. For example, in one embodiment, an assistant may be trained based on data collected from a single SME, a defined group of SMEs, and the like. Although healthcare embodiments are discussed herein as illustrative examples, these examples are not intended to be limiting, and the cognitive assistants described herein can be utilized in a variety of fields. Generally, embodiments of the present disclosure enable intelligent cognitive assistance in any field that ordinarily involves expert decision-making, including sequential decision-making (such as where the results of one decision affect the next decision).

In one embodiment of the present disclosure, a cognitive system identifies inflection points in a trajectory (such as in a patient's treatment or diagnosis path), as well as the corresponding SME decision during that time. For example, each time new data is available (e.g., results from a test, new symptomology, etc.), the cognitive system may identify this as a time that may require a decision from the healthcare provider. In an embodiment, this decision may include ordering one or more tests, making a diagnosis, continuing on the current plan, and the like. Based on these decisions, the cognitive system trains an imitation learning model. When a decision must be made for a subsequent patient, a user can provide the attributes or healthcare data of the subsequent patient to the cognitive system. The system can then generate one or more intelligent decisions, based on its imitation model(s).

FIG. 1 is a block diagram of a Cognitive Assistant Device 105, according to one embodiment disclosed herein. As illustrated, the Cognitive Assistant Device 105 includes a Processor 110, a Memory 115, Storage 120, and a Network Interface 125. In the illustrated embodiment, Processor 110 retrieves and executes programming instructions stored in Memory 115 as well as stores and retrieves application data residing in Storage 120. Processor 110 is representative of a single CPU, multiple CPUs, a single CPU having multiple processing cores, and the like. Memory 115 is generally included to be representative of a random access memory. Storage 120 may be a disk drive or flash-based storage device, and may include fixed and/or removable storage devices, such as fixed disk drives, removable memory cards, or optical storage, network attached storage (NAS), or storage area-network (SAN). Through the Network Interface 125, the Cognitive Assistant Device 105 may be communicatively coupled with other devices, including data stores containing electronic health records, terminals or devices used by healthcare providers, and the like.

In the illustrated embodiment, the Storage 120 includes multiple Electronic Health Records (EHRs) 160. In an embodiment, the EHRs 160 include any healthcare-related data corresponding to any number of patients. For example the EHRs 160 may include data about symptoms, treatments, diagnoses, test results, and other attributes of a patient (such as heart rate, blood pressure, age, weight, height, sex, and the like). Although illustrated as residing in Storage 120 on the Cognitive Assistant Device 105, in some embodiments, EHRs 160 may also or alternatively reside on one or more other databases or storage devices, such as in a cloud environment or at a remote facility. As illustrated, the Memory 115 includes a Cognitive Application 130, which is used to provide cognitive assistance to users.

The Cognitive Application 130 includes an EHR Analyzer 135, one or more Cognitive Models 140, and a Decision Component 155. Although depicted as distinct components for illustrative purposes, in embodiments, the functionality of the EHR Analyzer 135, Cognitive Models 140, and Decision Component 155 may be combined or divided into one or more other components, depending on the particular implementation. In an embodiment, the EHR Analyzer 135 receives EHRs 160, and processes them to identify inflection points in the data. As used herein, an inflection point refers to a moment or window in time where a decision is made. These inflection points may be points in a patient's treatment or diagnosis where the patient trajectory changed because of the input of a SME.

For example, in one embodiment, the EHR Analyzer 135 identifies decisions made by a healthcare provider (such as a doctor), and for each decision, identifies the state of the patient at that time. In an embodiment, the state of the patient includes any data or attributes of the patient that were present at the time of the decision. For example, in an embodiment, the patient state includes all attributes which the patient was currently exhibiting. In some embodiments, the patient state also includes previous attributes, whether or not the patient is currently exhibiting them. Further, in some embodiments, the patient state includes only attributes which were known to the healthcare provider at the time of the decision, such as symptoms, test results, and other attributes, but excludes attributes which were unknown by the provider. An attribute may be unknown because test results were not yet available, the decision-maker did not have access to the data, the patient was withholding information, and the like.

In another embodiment, the EHR Analyzer 135 identifies changes in the state of the patient, and determines what decision the healthcare provider made at that time. For example, in such an embodiment, the EHR Analyzer 135 may determine that each new visit constitutes a state change. Similarly, in an embodiment, the EHR Analyzer 135 may identify when the patient's symptoms, attributes, or test results change, and identify any corresponding decision made by the provider (which may include continuing the current path with no change in treatment, tests, or diagnosis). In yet another embodiment, the EHR Analyzer 135 may determine the patient's state at predefined intervals (e.g., every day, every week, and the like), and determine the decision(s) corresponding to each interval.

Once the states and corresponding decisions have been identified, the Cognitive Application 130 uses this data to train one or more Cognitive Models 140. In an embodiment, the Cognitive Model 140 is an imitation learning model. In one embodiment, a different Cognitive Model 140 is trained for each cohort or group of patients. For example, EHRs 160 from each patient may be used to train different models based on one or more attributes of the patient (such as age, sex, diagnoses, body mass index, and the like). In some embodiments, differing Cognitive Models 140 are trained based on the identity of the healthcare provider who provided the corresponding decision(s). For example, in one embodiment, a separate Cognitive Model 140 may be trained for each individual healthcare provider, in order to replicate the decision-making process of the individual provider. In one embodiment, a Cognitive Model 140 may be trained based on decisions from one or more identified groups of providers, such as all healthcare professionals in a particular facility. In some embodiments, the Cognitive Models 140 are trained based on decisions from more defined groups of healthcare providers, such as surgeons, doctors (including doctors with a particular specialty), or other delineations.

In the illustrated embodiment, the Cognitive Model 140 includes a Generator 145 and a Discriminator 150, which are discussed in more detail below. Generally, the Generator 145 receives the EHR 160 data, and generates a decision based on its current training, sometimes referred to as a policy. In one embodiment, the Generator 145 includes a deep neural network that models the distribution of expert trajectories by mapping from an observation space (e.g., the known attributes of the patient) to an action space (e.g., the decision(s) made by the expert). In an embodiment, the Discriminator 150 is also a neural network, and is used during a training or refinement phase for the Cognitive Model 140. In one embodiment, the Discriminator 150 compares the decision generated by the Generator 145 with the actual decision made by the SME. Based on this comparison, the Discriminator 150 updates or refines the Generator 145 (e.g., by adjusting the policy or weights of the Generator 145).

As illustrated, the Decision Component 155 is used during an operational phase of the Cognitive Application 130. For example, in one embodiment, the Decision Component 155 receives EHRs 160 for the index patient (e.g., the patient that is undergoing treatment, diagnosis, or is otherwise being considered by a healthcare provider), and uses the Cognitive Model 140 to generate a decision. In one embodiment, for example, the Cognitive Model 140 is trained using decisions from SMEs or highly trained individuals, and the Cognitive Application 130 is subsequently used by SMEs to aid their decision-making. In another embodiment, the Cognitive Application 130 is used by healthcare providers or individuals with less training or less expertise, in order to simulate the decision-making of a highly trained user. For example, if no SME is available for consultation, the Cognitive Application 130 can act as a substitute decision-maker, in some embodiments.

In one embodiment, the Cognitive Model 140 generates a confidence or probability for each of several potential decisions, and the Decision Component 155 ranks the potential decisions and selects one or more of the highest-ranked decisions. In some embodiments, the ranking of the decisions may be further based on the cost or availability of each decision, the invasiveness of the decision (e.g., whether the decision would require surgery or other invasive actions, or require additional detail or action from the patient), and the like.

In one embodiment, the Decision Component 155 selects a predefined number of decisions, based on their respective rankings. In another embodiment, the Decision Component 155 selects all decisions with a confidence score that exceed a predefined threshold. In some embodiments, the selected decisions are provided as suggestions to the user. In some embodiments, the decisions may be enacted by the Cognitive Application 130. In some embodiments, the Decision Component 155 may determine whether to enact the decision or to suggest it based on a variety of factors, such as the confidence value generated by the Cognitive Model 140, the invasiveness of the decision, the cost of implementing the decision, any applicable regulations or laws, and the like. For example, a decision to continue the current path (e.g., to do nothing) may be enacted without requiring approval, in some embodiments. Similarly, a decision that involves performing a relatively inexpensive test on a sample that has already been obtained may also be enacted without further approval in some embodiments, because it is inexpensive and non-invasive (as the sample has already been obtained). In contrast, a decision that may involve higher costs or more invasiveness may be provided to a user for approval. In some embodiments, however, all decisions must be approved prior to proceeding.

In one embodiment, the Cognitive Application 130 is used prior to diagnosis of a patient, in order to facilitate diagnosis. In such an embodiment, the generated decisions may include things like particular lab tests or examinations, which may aid a healthcare provider in gaining the relevant information more rapidly, and expedite the diagnosis process. In some embodiments, the Cognitive Application 130 is utilized post-diagnosis, during treatment of the patient. In one embodiment, different Cognitive Models 140 are utilized for the pre-diagnosis trajectory and the post-diagnosis treatment of the patient. In a post-diagnosis embodiment, the generated decisions may include, for example, suggested treatments at each inflection point.

In some embodiments, after providing one or more generated decisions, the Decision Component 155 may continue to monitor the EHRs 160 of the index patient. For example, the Cognitive Application 130 may subsequently determine that the result of the decision is available (e.g., the results of the suggested lab tests are found in one or more new EHRs 160). Based on this, the Cognitive Application 130 may determine that the patient's state has changed (e.g., because new data is available), and the Decision Component 155 may automatically generate one or more new decisions based on this updated state (such as suggesting new lab tests). Alternatively, in some embodiments, a user may prompt the Cognitive Application 130 to generate a new decision. In this way, the Cognitive Application 130 can facilitate and expedite diagnosis or treatment of a patient, by repeatedly evaluating the trajectory and attributes of the patient based on prior training.

Advantageously, embodiments of the present disclosure enable cognitive analysis of EHRs 160 based on prior SME decisions. This improves whatever field the Cognitive Application 130 is employed in, by providing intelligent and dynamic decisions based on a huge amount of data. These decisions may supplement a present SME, in order to aid his or her decision-making process. Similarly, in embodiments, the Cognitive Application 130 can be used to partially replace the need for an SME at each inflection point in the trajectory. For example, in more rural or disconnected areas, medical experts may be relatively rare or difficult to consult. Similar problems may exist during non-business hours, or with patients who may be unable to acquire repeated access to a highly trained expert (for example, due to cost, convenience, and the like). In such instances, embodiments of the present disclosure can enable a non-expert, an expert with less training or expertise in the domain, or a non-expert to nevertheless continue the diagnosis trajectory by relying on decision-making of the Cognitive Application 130. In this way, a diagnosis can be identified more rapidly and with fewer resources (e.g., utilizing less time of highly-trained experts). Additionally, these decisions are objective, unlike traditional expert decision-making, which can improve overall results.

Similarly, embodiments of the present disclosure improve the functioning of computing devices themselves by enabling functionality that was not previously possible with known solutions. Embodiments disclosed herein enable a computer to generate intelligent and cognitively-driven decisions for complex problems, in a responsive and rapid manner that has not heretofore been accomplished. This greatly improves the operational capabilities of the computing device, and allows the computer to assume a more important and active role in the process.

Figure 2:
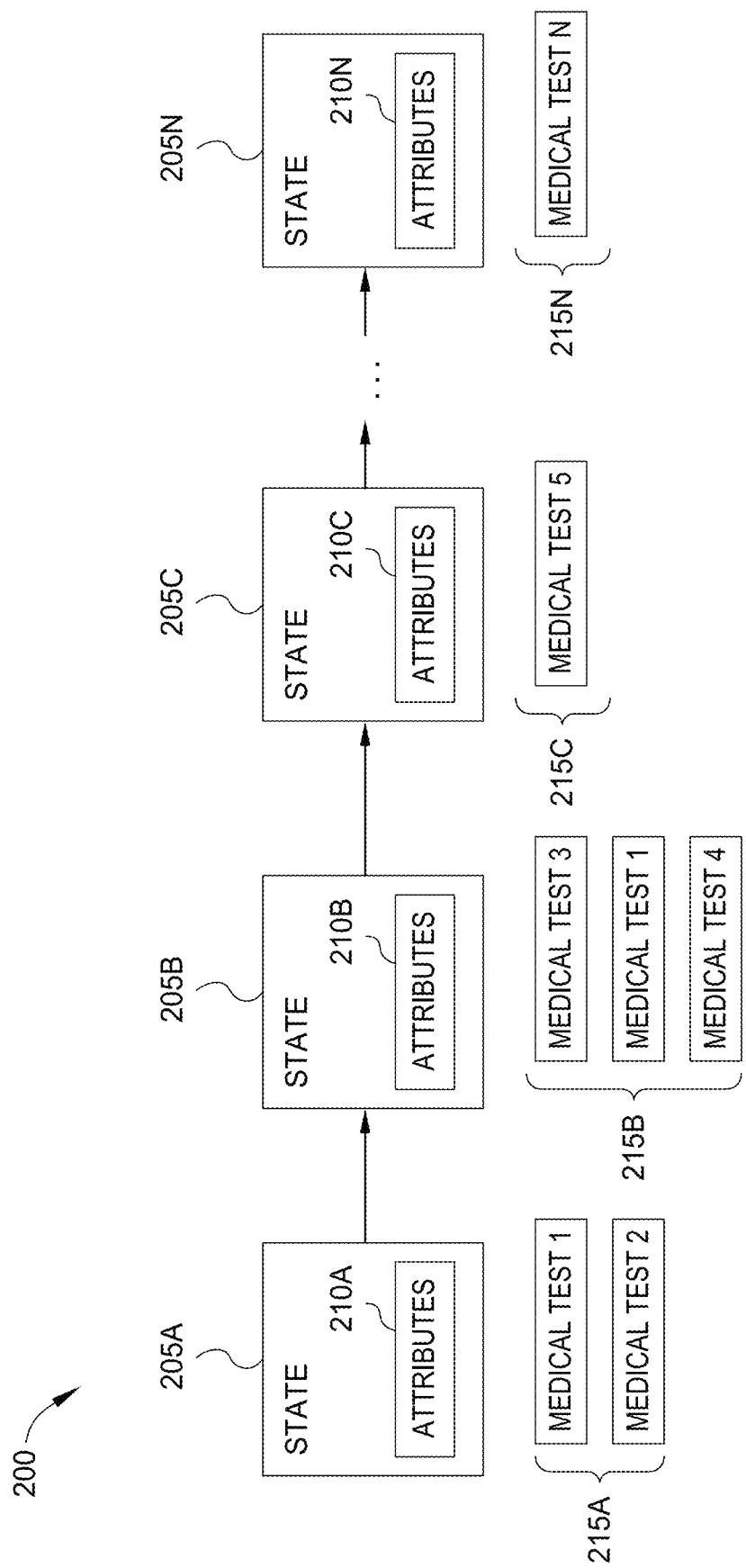
FIG. 2 is a flow diagram illustrating a trajectory, including transitions between states and corresponding expert decisions, according to one embodiment disclosed herein.

FIG. 2 is a flow diagram illustrating a Trajectory 200, including transitions between States 205 and corresponding expert Decisions 215, according to one embodiment disclosed herein. In the illustrated Trajectory 200, each State 205 is associated with a number of Attributes 210 associated with that State 205. For example, in a healthcare setting, the Attributes 210 may include the patient's gender, sex, age, weight, height, any symptoms or complaints at the time, the results of any tests that have been completed (e.g., blood test, urinalyses, DNA tests, etc.), and the like. Further, in the illustrated embodiment, each Decision 215 includes one or more medical tests (such as laboratory tests) to be completed. In one embodiment, each State 205 is defined by its Attributes 210. That is, in one embodiment, each time one or more Attributes 210 change, the State 205 also changes, even if no Decision 215 has been made. In such an embodiment, the Decision 215 may be equated to "no decision" or "no change." In another embodiment, each State 205 is defined by the Decision(s) 215 that immediately preceded and/or followed the State 205. That is, in one embodiment, rather than utilizing a change in Attributes 210 to define state transitions, the Cognitive Application 130 utilizes the expert Decisions 215 to define transitions between States 205 in the Trajectory 200.

In the illustrated embodiment, a first State 205A is associated with a set of Attributes 210A. In response to these Attributes 210A, an SME made a Decision 215A that included ordering two tests, Medical Test 1 and Medical Test 2. At some subsequent time, the patient was in State 205B, associated with Attribute 210B. In response to these Attributes 210B, the SME made Decision 215B, which included Medical Test 3, Medical Test 1, and Medical Test 4. That is, the SME decided to get an updated result for the Medical Test 1, and also ordered separate tests that had not been run before. As further illustrated, when the patient was in State 205C, associated with Attributes 210C, the healthcare provider made Decision 215C. As illustrated, these States 205A-N and Decisions 215A-N can go on for any number of states and decisions, and for any period of time. In one embodiment, the Trajectory 200 terminates with a final diagnosis. In a treatment embodiment, the Trajectory 200 may terminate when the patient is cured, in remission, stable, and the like.

In one embodiment, when training the Cognitive Application 130, an expert Decision 215 is defined as a set of decisions (e.g., a set of medical tests or treatments). In another embodiment, each separate order (e.g., each separate medical test, or each distinct treatment) is treated as an independent Decision 215 when training the Cognitive Application 130. In this way, the Cognitive Application 130 may be trained to either generate individual decisions with corresponding confidence, or sets or groups of decisions with an overall confidence for the entire group. In some embodiments, the Cognitive Application 130 is trained in both ways, so as to present comprehensive plans (including multiple suggestions at each inflection point) as well as individual decisions, if the provider does not wish to implement the entire plan.

As illustrated, the Trajectory 200 can proceed through any number of States 205 and Decisions 215. Each independent Decision 215 can be used to train one or more Cognitive Models 140. Further, although a Trajectory 200 for a single patient is illustrated, in embodiments, Trajectories 200 from many different patients may be utilized to train the same Cognitive Model 140. Further, in some embodiments, as discussed above, the Attributes 210 of the particular patient may be considered when determining which Cognitive Model 140 to train. In one embodiment, a single patient's data may be used to train differing Cognitive Models 140 (e.g., corresponding to differing cohorts) depending on the patient's particular Attributes 210 (e.g., the particular cohort the patient belonged to) to at the time the corresponding Decision 215 was made.

Figure 3:
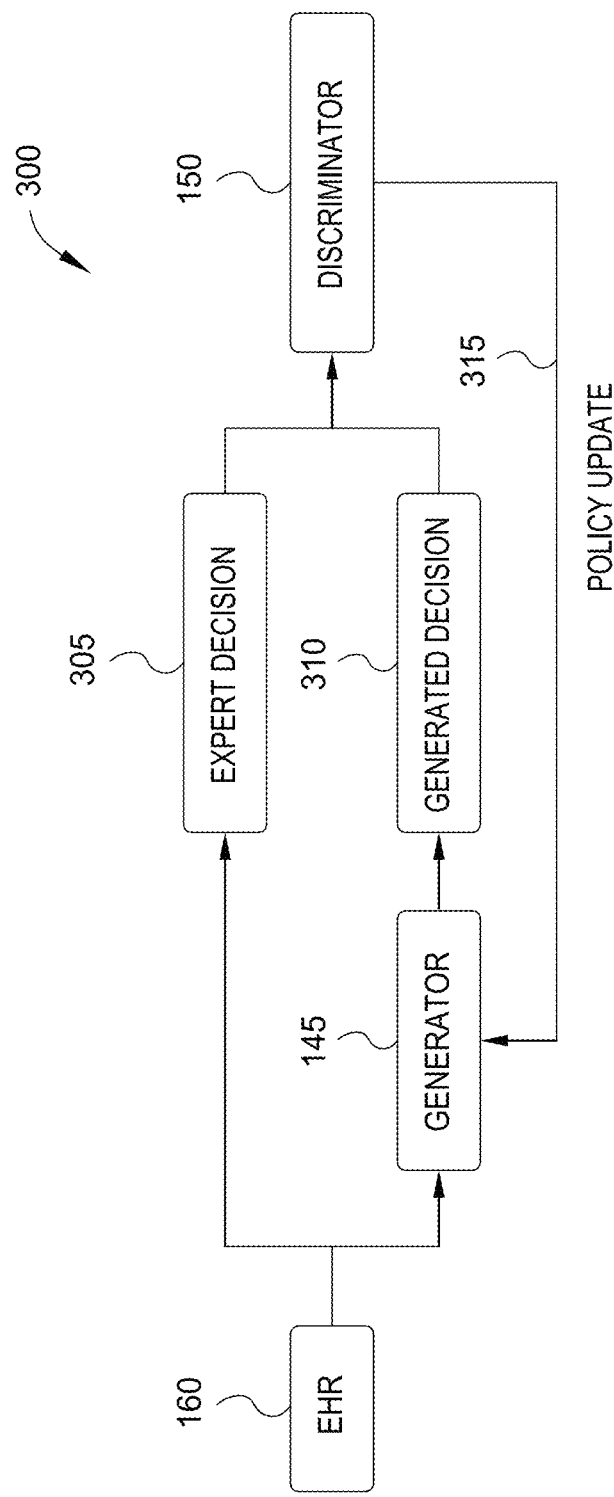
FIG. 3 is a flow diagram illustrating a workflow for training a cognitive assistant to aid decision-making, according to one embodiment disclosed herein.

FIG. 3 is a flow diagram illustrating a Workflow 300 for training a cognitive assistant to aid decision-making, according to one embodiment disclosed herein. In the illustrated workflow 300, data extracted from EHRs 160, which were used by an SME to generate an Expert Decision 305, are provided to the Generator 145. The Generator 145 then generates a Generated Decision 310 (also referred to as a training decision) based on processing the attributes reflected in the EHR 160 with an imitation model (such as a deep neural network). As illustrated, the Discriminator 150 then compares the Expert Decision 305 and the Generated Decision 310. In one embodiment, the Cognitive Assistant Device 105 utilizes generative adversarial imitation learning (GAIL). In one embodiment, this involves training two deep neural networks, one for the Generator 145 and one for the Discriminator 150.

As illustrated, based on this comparison, the Discriminator 150 transmits a Policy Update 315 to the Generator 145. In this way, the Generator 145 is refined and modified based on the differences between the Generated Decision 310 and the Expert Decision 305. In an embodiment, during training, the Generator 145 attempts to generate expert decisions, and the Discriminator 150 attempts to differentiate between the Expert Decision 305 and the Generated Decision 310. In such an embodiment, the Policy Update 315 may include a determined step along the gradient. At convergence, the Discriminator 150 can no longer distinguish between the Expert Decisions 305 and the Generated Decisions 315, and the model is fully trained.

In some embodiments, the Cognitive Model 140 is further refined during use. For example, in one embodiment, the Cognitive Model 140 may periodically (e.g., every day, every hour, etc.) identify new exemplars (e.g., new expert decisions), and refine the Generator 145 based on these decisions. In another embodiment, the Cognitive Model 140 may continuously monitor the EHRs 160 to identify new exemplar decisions, and undergo training or refinement once these exemplars are identified. In one embodiment, each exemplar is provided the same weight as all other exemplars. In some embodiments, however, different exemplars may be afforded differing weight. For example, in one embodiment, decisions from a particular SME may be weighted higher than another SME, or more recent decisions may be afforded increased weight.

Figure 4:
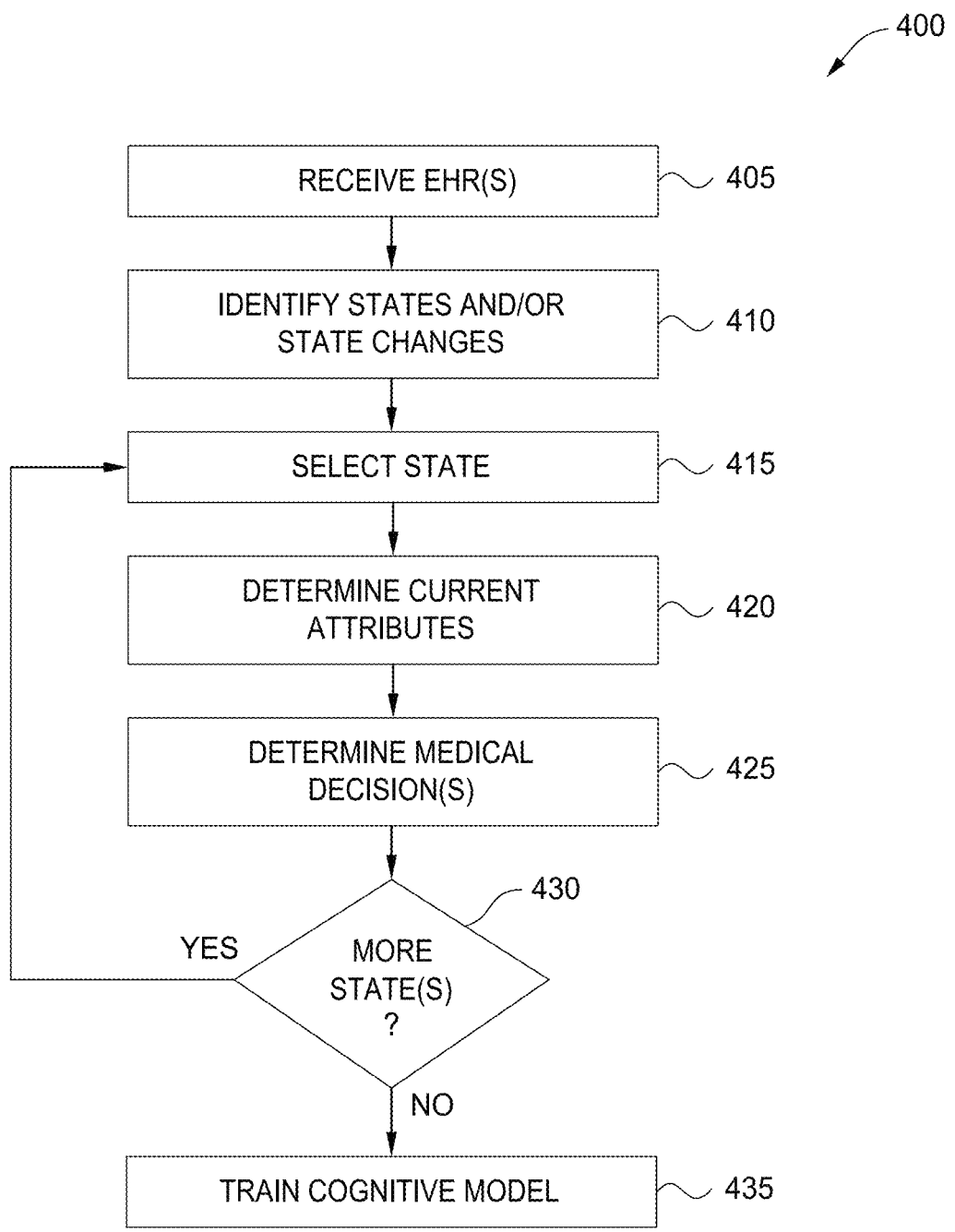
FIG. 4 is a flow diagram illustrating a method for training a cognitive assistant to aid decision-making, according to one embodiment disclosed herein.

FIG. 4 is a flow diagram illustrating a method 400 for training a cognitive assistant to aid decision-making, according to one embodiment disclosed herein. The method 400 begins at block 405, where the Cognitive Application 130 receives EHRs from any source. In some embodiments, the EHRs to train the Cognitive Application 130 may be specified by a user or administrator. In another embodiment, the Cognitive Application 130 may itself identify EHRs that are accessible for training purposes. The method 400 then proceeds to block 410, where the EHR Analyzer 135 identifies states and/or state changes reflected in the EHR data. For example, as discussed above, in one embodiment, the EHR Analyzer 135 identifies each expert decision (where each decision reflects a state change). In another embodiment, the EHR Analyzer 135 identifies states and state changes based on the patient attributes (and changes in those attributes) reflected in the EHR.

The method 400 continues to block 415, where the EHR Analyzer 135 selects one of the states (which may be identified directly, or may be identified based on the determined state changes or decisions). At block 420, the EHR Analyzer 135 determines the current attributes reflected in the EHRs associated with the selected state. For example, in one embodiment, the EHR Analyzer 135 determines a window of time covered by the current state, and identifies any patient attributes that were present during this time. In one embodiment, the EHR Analyzer 135 identifies attributes that were first reflected in one or more EHRs during the time period. In some embodiments, the EHR Analyzer 135 also identifies attributes that were first identified prior to the beginning of the window, unless the EHRs indicate that the attribute was no longer present during the window.

In one embodiment, the EHR Analyzer 135 determines, for the selected state, which patient attributes were known to the SME who made the corresponding decision. That is, in one embodiment, rather than considering all attributes reflected in the EHRs, the EHR Analyzer 135 determines, for each attribute, whether this data was available to or known by the SME who made the expert decision. For example, if a healthcare provider requested a laboratory test be conducted, the EHR Analyzer 135 may determine what data was considered by the provider in making this decision. If the healthcare provider only had access to certain EHRs, for example, the EHR Analyzer 135 may rely on only these EHRs. Similarly, in some embodiments, the healthcare provider may indicate which EHRs or which attributes he or she was relying on in making the decision. In such an embodiment, the EHR Analyzer 135 can identify this particular data for training purposes. Further, although a patient may actually possess a particular attribute during the window, this attribute may be unknown because of, for example, obfuscation by the patient, delayed tests, and the like. In one embodiment, in order to determine what was known at the time of the decision, the EHR Analyzer 135 considers only EHRs that were recorded during or before the decision, and does not consider subsequent data, even if it refers back to the prior window of time.

The method 400 then proceeds to block 425, where the EHR Analyzer 135 determines which decision(s) the SME made in response to the selected state (e.g., in response to the attributes reflected in the selected state). In an embodiment, these decisions may include ordering medical tests, diagnoses, treatments, and the like. At block 430, the EHR Analyzer 135 determines whether there are additional states in the EHRs that have yet to be considered. If so, the method 400 returns to block 415. If not, the method 400 proceeds to block 435, where the Cognitive Model 140 is trained on the data, as discussed above. In some embodiments, the method 400 is repeated for each available EHR. In some embodiments, the method 400 is repeated for each patient, and multiple EHRs may be identified and considered for each state and decision.

In some embodiments, as discussed above, multiple Cognitive Models 140 are trained based on EHRs from various patients. In one embodiment, the EHR Analyzer 135 determines which Cognitive Model 140 the data should be applied to, based on the attributes of the corresponding patient, the treating SME, and the like. For example, in one embodiment, a different Cognitive Model 140 is trained based on decisions from a particular SME, experts belonging to or associated with a particular institution (e.g., a particular clinic or hospital), a particular geographic region, a particular medical specialty, and the like. Similarly, in one embodiment, different Cognitive Models 140 are trained based on the patient's attributes, patient cohort, diagnoses, and the like.

Figure 5:
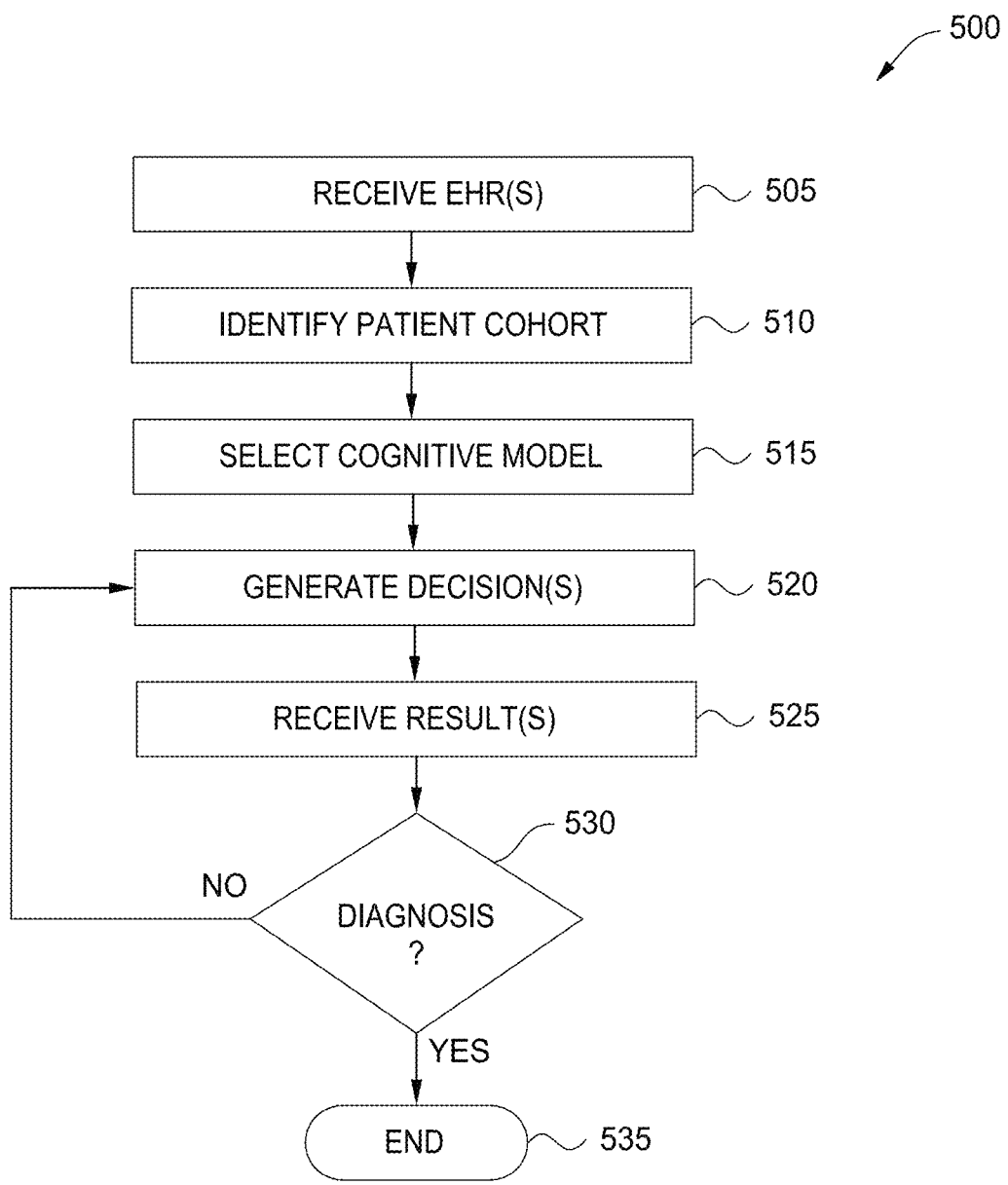
FIG. 5 is a flow diagram illustrating a method for cognitive decision-making with an assistant, according to one embodiment disclosed herein.

FIG. 5 is a flow diagram illustrating a method 500 for cognitive decision-making with an assistant, according to one embodiment disclosed herein. In the illustrated embodiment, the method 500 begins at block 505, where the Cognitive Application 130 receives one or more EHRs associated with the index patient (e.g., the patient to be diagnosed or treated). At block 510, the Decision Component 155 identifies a patient cohort associated with the index patient. For example, the Decision Component 155 may identify a cohort based on attributes of the patient, such as age, weight, and any other applicable attributes. At block 515, the Decision Component 155 selects a Cognitive Model 140 to use in aiding decision-making for the index patient.

As discussed above, in some embodiments, the Decision Component 155 selects a Cognitive Model 140 based in part on the cohort of the index patient. In some embodiments, the Decision Component 155 also considers various other factors, such as the geographic location of the patient, the treating physician, a suspected or diagnosed illness, and the like. In embodiments, the Decision Component 155 can select a Cognitive Model 140 using any appropriate methodology. The method 500 then proceeds to block 520, where the Decision Component 155 uses the selected Cognitive Model 140 to generate one or more decisions, based on processing the received EHRs with the selected Cognitive Model 140.

In one embodiment, the Cognitive Model 140 also generates a confidence measure for each decision. In such an embodiment, the Decision Component 155 can rank the decisions based on these confidence measures. In one embodiment, the Decision Component 155 selects one or more of the generated decisions based on this ranking. For example, in one embodiment, the Decision Component 155 selects the N best decisions, where N may be defined by a user or administrator. Similarly, in another embodiment, the Decision Component 155 selects the decisions with confidence measures that exceed a predefined threshold, which may also be defined by a user or administrator. In one embodiment, the Decision Component 155 presents the selected decisions as suggestions to the user, such as via a graphical user interface (GUI).

In some embodiments, the Decision Component 155 can implement one or more decisions based on various factors discussed above. For example, in one embodiment, the Decision Component 155 may implement decisions with confidence measures exceeding a threshold. In one embodiment, the Decision Component 155 may first determine other factors, such as the cost or invasiveness of the decision, prior to implementing it. In other embodiments, the user may select one or more of the decisions for implementation. In the illustrated embodiment, the method 500 is used for pre-diagnosis testing. In embodiments, however, the Cognitive Application 130 can be used to aid other decision-making trajectories, such as treatment of a patient.

At block 525, the Decision Component 155 receives results of the generated decisions. For example, if a decision included ordering a lab test, and the lab test is actually ordered and completed, the Decision Component 155 can receive the results of this test. Similarly, in a treatment embodiment, the Decision Component 155 may receive an indication as to whether the treatment was successful. At block 530, the Decision Component 155 determines whether the patient has been diagnosed. That is, the Decision Component 155 determines whether a healthcare provider has diagnosed the patient's disorder. If so, the method 500 terminates at block 535. If not, the method 500 returns to block 520, where the Decision Component 155 generates one or more new decisions, based on this updated medical data (e.g., the patient's EHRs, including the newly-received results from the prior tests). In this way, the method 500 can be used to enable iterative decision-making. The Cognitive Application 130 can thus help shape the patient trajectory from initial meeting to eventual diagnosis.

Although a diagnostic embodiment is illustrated in FIG. 5, in embodiments, the method 500 may also be used for treatment, or for other decision-making trajectories (including non-medical trajectories). For example, in a treatment embodiment, the block 530 may be replaced with a determination as to whether the treatment is complete (e.g., the patient has been cured, is in remission, is stable, or otherwise meets predefined criteria to terminate the method 500). Generally, the decision block 530 can represent any defined criteria for the termination of the decision-making trajectory, depending on the particular field and implementation. In an embodiment, this termination criterion is defined by a user or administrator when designing the system, or when utilizing the Cognitive Application 130 in operation.

Figure 6:
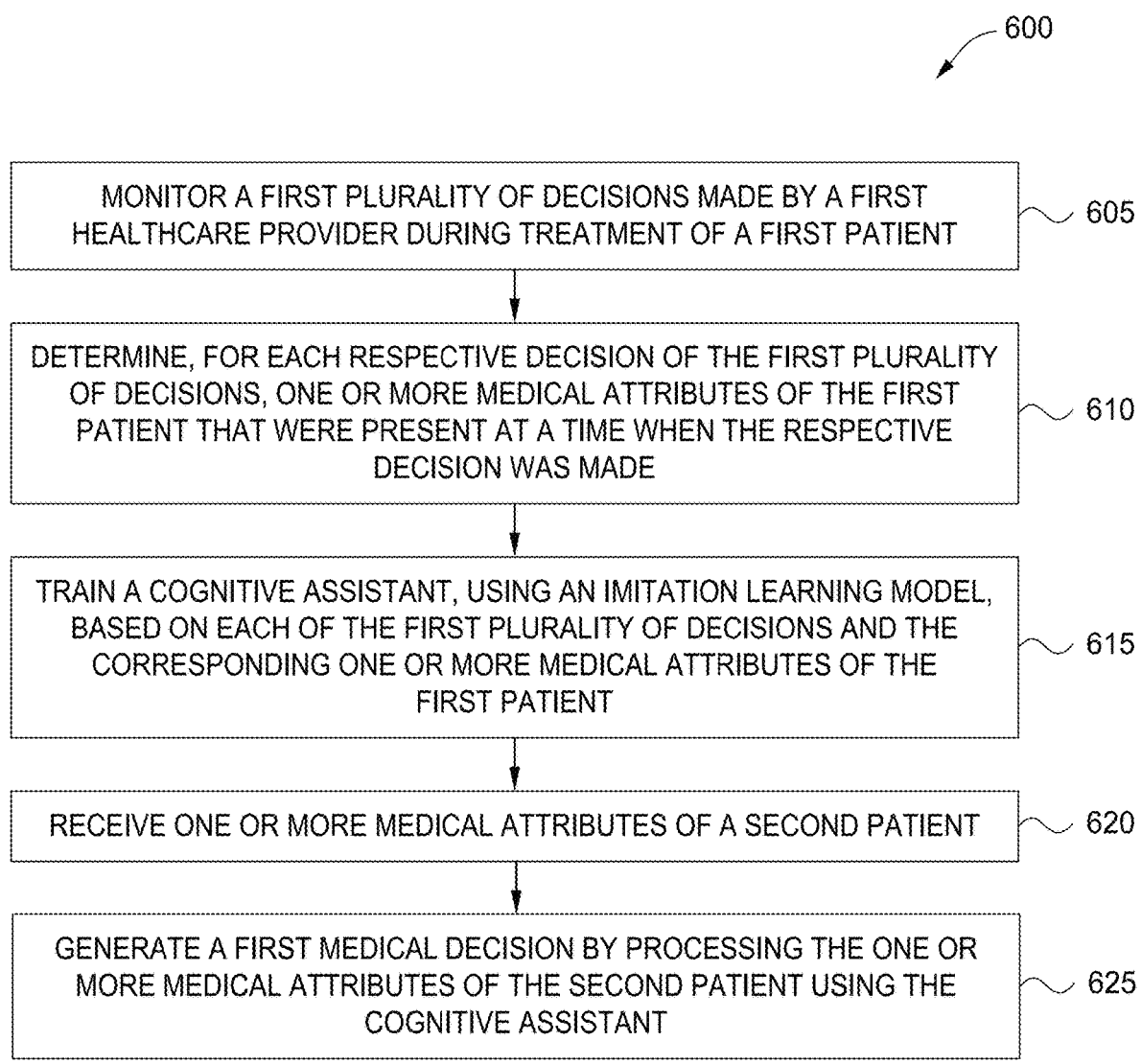
FIG. 6 is a flow diagram illustrating a method for utilizing a cognitive assistant to aid decision-making, according to one embodiment disclosed herein.

FIG. 6 is a flow diagram illustrating a method 600 for utilizing a cognitive assistant to aid decision-making, according to one embodiment disclosed herein. The method 600 begins at block 605, where the Cognitive Application 130 monitors a first plurality of decisions made by a first healthcare provider during treatment of a first patient. At block 610, the Cognitive Application 130 determines, for each respective decision of the first plurality of decisions, one or more medical attributes of the first patient that were present at a time when the respective decision was made. The method 600 then continues to block 615, where the Cognitive Application 130 trains a cognitive assistant, using an imitation learning model, based on each of the first plurality of decisions and the corresponding one or more medical attributes of the first patient. Further, at block 620, the Cognitive Application 130 receives one or more medical attributes of a second patient. Finally, the method 600 continues to block 625, where the Cognitive Application 130 generates a first medical decision by processing the one or more medical attributes of the second patient using the cognitive assistant.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Cognitive Application 130) or related data available in the cloud. For example, the Cognitive Application 130 could execute on a computing system in the cloud and train Cognitive Models 140 based on EHRs 160. In such a case, the Cognitive Application 130 could generate intelligent decisions and store data at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   evaluating electronic health records of a first patient to identify state changes, wherein each respective state change corresponds to a point in time when one or more medical attributes of the first patient changed;
   identifying, in the electronic health records, a first plurality of decisions made by a first healthcare provider during treatment of the first patient, wherein each respective decision of the plurality of decisions corresponds to a respective state change, and wherein at least a first decision of the plurality of decisions corresponds to the first healthcare provider taking no action and continuing with a treatment plan in response to a state change;
   determining, for each respective decision of the first plurality of decisions, one or more corresponding medical attributes of the first patient that were present at a time when the respective decision was made;
   generating a trajectory for the first patient, wherein the trajectory reflects the plurality of decisions and, for each respective decision of the first plurality of decisions, the corresponding medical attributes;
   training a cognitive assistant, using a generative adversarial imitation learning (GAIL) model, based on the trajectory, comprising:

training a generator neural network to generate medical decisions based on the trajectory, comprising:
weighting each respective decision of the first plurality of decisions based at least in part on recency of each respective decision, wherein more recent decisions are provided with increased weight; and
weighting each respective decision of the first plurality of decisions based on a respective subject matter expert (SME) that made the respective decision, wherein a higher weight is provided for a first set of decisions of the first plurality of decisions, as compared to a weight provided for a second set of decisions of the first plurality of decisions, based on determining that the first set of decisions were made by a particular SME and the second set of decisions were made by a different SME, wherein both the first set of decisions and the second set of decisions are used to train the generator neural network; and
training a discriminator neural network to differentiate between generated medical decisions and the first plurality of decisions;
receiving one or more medical attributes of a second patient; and
generating a first medical decision by processing the one or more medical attributes of the second patient using the cognitive assistant.

2. The method of claim 1, wherein monitoring the plurality of decisions made by the first healthcare provider comprises analyzing electronic health records (EHR) of the first patient to identify each of the first plurality of decisions.

3. The method of claim 1, wherein generating the first medical decision is performed upon determining that a cohort of the second patient matches a cohort of the first patient.

4. The method of claim 3, the method further comprising:
receiving one or more medical attributes of a third patient;
upon determining that a cohort of the third patient does not match the cohort of the first patient, identifying a second cognitive assistant that was trained for the cohort of the third patient; and
generating a second medical decision by processing the one or more medical attributes of the third patient using the second cognitive assistant.

5. The method of claim 1, wherein generating the first medical decision comprises suggesting a first lab test for the second patient.

6. The method of claim 5, the method further comprising:
receiving a first result for the first lab test for the second patient; and
generating a second medical decision by processing the first result using the cognitive assistant, wherein generating the second medical decision comprises suggesting a second lab test for the second patient.

7. The method of claim 1, wherein training a cognitive assistant comprises, for each respective decision of the first plurality of decisions:
generating a training decision by providing the corresponding one or more medical attributes of the first patient that were present at the time when the respective decision was made to the cognitive assistant;
identifying the respective decision; and
refining the cognitive assistant based on comparing the training decision with the respective decision.

8. The method of claim 1, wherein the cognitive assistant is trained based on medical decisions by the first healthcare provider with respect to a plurality of patients.

9. The method of claim 1, wherein the cognitive assistant is further trained based on medical decisions by a plurality of healthcare providers with respect to a plurality of patients.

10. A computer program product comprising:
a computer-readable storage medium having computer-readable program code embodied therewith, the computer-readable program code executable by one or more computer processors to perform an operation comprising:
evaluating electronic health records of a first patient to identify state changes, wherein each respective state change corresponds to a point in time when one or more medical attributes of the first patient changed;
identifying, in the electronic health records, a first plurality of decisions made by a first healthcare provider during treatment of the first patient, wherein each respective decision of the plurality of decisions corresponds to a respective state change, and wherein at least a first decision of the plurality of decisions corresponds to the first healthcare provider taking no action and continuing with a treatment plan in response to a state change;
determining, for each respective decision of the first plurality of decisions, one or more corresponding medical attributes of the first patient that were present at a time when the respective decision was made;
generating a trajectory for the first patient, wherein the trajectory reflects the plurality of decisions and, for each respective decision of the first plurality of decisions, the corresponding medical attributes;
training a cognitive assistant, using a generative adversarial imitation learning (GAIL) model, based on the trajectory, comprising:
training a generator neural network to generate medical decisions based on the trajectory, comprising:
weighting each respective decision of the first plurality of decisions based on a respective subject matter expert (SME) that made the respective decision, wherein a higher weight is provided for a first set of decisions of the first plurality of decisions, as compared to a weight provided for a second set of decisions of the first plurality of decisions, based on determining that the first set of decisions were made by a particular SME and the second set of decisions were made by a different SME, wherein both the first set of decisions and the second set of decisions are used to train the generator neural network; and
weighting each respective decision of the first plurality of decisions based on a respective subject matter expert (SME) that made the respective decision, wherein a higher weight is provided for a first set of decisions of the first plurality of decisions, as compared to a weight provided for a second set of decisions of the first plurality of decisions, based on determining that the first set of decisions were made by a particular SME and the second set of decisions were made by a different SME, wherein both the first set of decisions and the second set of decisions are used to train the generator neural network; and
training a discriminator neural network to differentiate between generated medical decisions and the first plurality of decisions;

receiving one or more medical attributes of a second patient; and generating a first medical decision by processing the one or more medical attributes of the second patient using the cognitive assistant.

11. The computer program product of claim 10, wherein generating the first medical decision is performed upon determining that a cohort of the second patient matches a cohort of the first patient.

12. The computer program product of claim 11, the operation further comprising:

receiving one or more medical attributes of a third patient;

upon determining that a cohort of the third patient does not match the cohort of the first patient, identifying a second cognitive assistant that was trained for the cohort of the third patient; and generating a second medical decision by processing the one or more medical attributes of the third patient using the second cognitive assistant.

13. The computer program product of claim 10, wherein generating the first medical decision comprises suggesting a first lab test for the second patient.

14. The computer program product of claim 13, the operation further comprising:

receiving a first result for the first lab test for the second patient; and generating a second medical decision by processing the first result using the cognitive assistant, wherein generating the second medical decision comprises suggesting a second lab test for the second patient.

15. The computer program product of claim 10, wherein training a cognitive assistant comprises, for each respective decision of the first plurality of decisions:

generating a training decision by providing the corresponding one or more medical attributes of the first patient that were present at the time when the respective decision was made to the cognitive assistant;

identifying the respective decision; and refining the cognitive assistant based on comparing the training decision with the respective decision.

16. A system comprising:

one or more computer processors; and a memory containing a program which when executed by the one or more computer processors performs an operation, the operation comprising:

evaluating electronic health records of a first patient to identify state changes, wherein each respective state change corresponds to a point in time when one or more medical attributes of the first patient changed;

identifying, in the electronic health records, a first plurality of decisions made by a first healthcare provider during treatment of the first patient, wherein each respective decision of the plurality of decisions corresponds to a respective state change, and wherein at least a first decision of the plurality of decisions corresponds to the first healthcare provider taking no action and continuing with a treatment plan in response to a state change;

determining, for each respective decision of the first plurality of decisions, one or more corresponding medical attributes of the first patient that were present at a time when the respective decision was made;

generating a trajectory for the first patient, wherein the trajectory reflects the plurality of decisions and, for each respective decision of the first plurality of decisions, the corresponding medical attributes;

training a cognitive assistant, using a generative adversarial imitation learning (GAIL) model, based on the trajectory, comprising:

training a generator neural network to generate medical decisions based on the trajectory, comprising:

weighting each respective decision of the first plurality of decisions based on a respective subject matter expert (SME) that made the respective decision, wherein a higher weight is provided for a first set of decisions of the first plurality of decisions, as compared to a weight provided for a second set of decisions of the first plurality of decisions, based on determining that the first set of decisions were made by a particular SME and the second set of decisions were made by a different SME, wherein both the first set of decisions and the second set of decisions are used to train the generator neural network; and weighting each respective decision of the first plurality of decisions based on a respective subject matter expert (SME) that made the respective decision, wherein a higher weight is provided for a first set of decisions of the first plurality of decisions, as compared to a weight provided for a second set of decisions of the first plurality of decisions, based on determining that the first set of decisions were made by a particular SME and the second set of decisions were made by a different SME, wherein both the first set of decisions and the second set of decisions are used to train the generator neural network; and training a discriminator neural network to differentiate between generated medical decisions and the first plurality of decisions;

receiving one or more medical attributes of a second patient; and generating a first medical decision by processing the one or more medical attributes of the second patient using the cognitive assistant.

17. The system of claim 16, wherein generating the first medical decision is performed upon determining that a cohort of the second patient matches a cohort of the first patient, the operation further comprising:

receiving one or more medical attributes of a third patient;

upon determining that a cohort of the third patient does not match the cohort of the first patient, identifying a second cognitive assistant that was trained for the cohort of the third patient; and generating a second medical decision by processing the one or more medical attributes of the third patient using the second cognitive assistant.

18. The system of claim 16, wherein generating the first medical decision comprises suggesting a first lab test for the second patient.

19. The system of claim 18, the operation further comprising:

receiving a first result for the first lab test for the second patient; and generating a second medical decision by processing the first result using the cognitive assistant, wherein generating the second medical decision comprises suggesting a second lab test for the second patient.

20. The system of claim 16, wherein training a cognitive assistant comprises, for each respective decision of the first plurality of decisions:

generating a training decision by providing the corresponding one or more medical attributes of the first patient that were present at the time when the respective decision was made to the cognitive assistant;
identifying the respective decision; and
refining the cognitive assistant based on comparing the training decision with the respective decision.

* * * * *